United States Patent [19]

Jäger

[11] B 4,002,657

[45] Jan. 11, 1977

[54] PERFLUOROALKYLALKYLCARBOXYLIC ACIDS, PROCESS FOR THEIR MANUFACTURE AND THEIR USE

[75] Inventor: Horst Jäger, Bettingen, Switzerland

[73] Assignee: Ciba-Geigy Corporation, Ardsley, N.Y.

[22] Filed: Feb. 15, 1974

[21] Appl. No.: 442,953

[44] Published under the second Trial Voluntary Protest Program on March 23, 1976 as document No. B 442,953.

[30] Foreign Application Priority Data

Mar. 5, 1973 Switzerland ............... 3184/73

[52] U.S. Cl. .................. 260/408; 260/465.7; 252/56 S
[51] Int. Cl.² .............. C07C 53/34; D06M 13/20
[58] Field of Search ............. 260/408, 539 R

[56] References Cited

UNITED STATES PATENTS

| | | | |
|---|---|---|---|
| 2,951,051 | 8/1960 | Tiers | 260/23 |
| 3,016,406 | 1/1962 | Brace | 260/653 |
| 3,106,589 | 10/1963 | Hauptschein et al. | 260/653.3 |
| 3,641,083 | 2/1972 | Anello et al. | 260/438.5 C |

FOREIGN PATENTS OR APPLICATIONS

| | | |
|---|---|---|
| 696,239 | 10/1964 | Canada |
| 2,070,452 | 9/1971 | France |
| 1,916,669 | 3/1970 | Germany |
| 2,104,750 | 2/1971 | Germany |

Primary Examiner—R. Gallagher
Assistant Examiner—Diana G. Rivers
Attorney, Agent, or Firm—Joseph G. Kolodny; Prabodh I. Almaula; Edward McC. Roberts

[57] ABSTRACT

New perfluoroalkylalkylcarboxylic acids of the formula

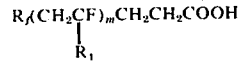

are provided, wherein $R_f$ is an unbranched or branched perfluoroalkyl radical with 3 to 18 carbon atoms, $R_1$ is hydrogen or fluorine and m is a whole number from 1 to 3.

The new compounds are suitable for producing water and oil-repellent finishes, soil-release and antisoiling effects on porous and non-porous substrates. They are further valuable intermediates for the manufacture of fluorinated compounds which may be used in the same field as the inventive compounds.

6 Claims, No Drawings

PERFLUOROALKYLALKYLCARBOXYLIC ACIDS, PROCESS FOR THEIR MANUFACTURE AND THEIR USE

French Pat. No. 2.070.452 teaches the manufacture of perfluoroalkylalkylcarboxylic acids by hydrolysis of corresponding nitriles according to the following reaction equation:

$$C_nF_{2n+1}(CH_2)_aCN + H_2O \rightarrow C_nF_{2n+1}(CH_2)_aCOOH + NH_3$$

The present invention provides new perfluoroalkylalkylcarboxylic acids of the formula

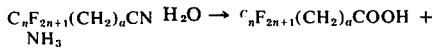  (1)

wherein $R_f$ is an unbranched or branched perfluoroalkyl radical with 3 to 18 carbon atoms, $R_1$ is hydrogen or fluorine, and m is a whole number from 1 to 3.

The unbranched or branched perfluoroalkyl radical can have e.g. the following formulae:

| | |
|---|---|
| $F(CH_2)_p-$ | $p = -3 - 18$ |
| $(CF_3)_2CF(CF_2)_q-$ | $q = 1 - 15$ |
| $CF_3[CF_2CF(CF_3)]_r-$ | $r = 1 - 5$ |
| $(CF_3)_2CF[CF_2CF(CF_3)]_s-$ | $s = 1 - 5$ |

Preferably the perfluoroalkyl radicals contain from 3 to 14 or from 4 to 12 carbon atoms, e.g. $C_4F_9$, $C_6F_{13}$, $C_8F_{17}$, $C_{10}F_{21}$, $C_{12}F_{25}$ or $(CF_3)_2CF(CF_2)_{q'}$-, wherein $q'$ is a whole number from 1 to 9.

$R_1$ is hydrogen or fluorine, preferably fluorine, and m is a whole number from 1 to 3, preferably 1.

The perfluoroalkylalkylcarboxylic acids according to the invention preferably have the formula

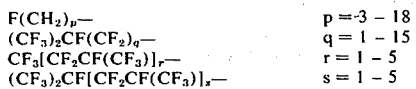  (2)

wherein R is hydrogen or fluorine, n is a whole number from 3 to 14, and m is a whole number from 1 to 3.

Particularly suitable are also the acids of the formulae

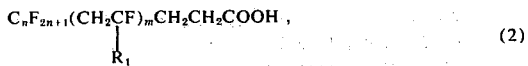  (3)

  (4)

$C_{n1}F_{2n1+1}CH_2CF_2CH_2CH_2COOH,$  (5)

$C_{n1}F_{2n1+1}CH_2CHF\ CH_2CH_2COOH,$  (6)

$C_{n1}F_{2n1+1}(CH_2CF_2)_2CH_2CH_2COOH$ and  (7)

$C_{n1}F_{2n1+1}(CH_2CHF)_2CH_2CH_2COOH,$  (8)

wherein $R_1$ is hydrogen or fluorine, $n_1$ is a whole number from 4 to 12, preferably from 6 to 10, and m is a whole number from 1 to 3.

The perfluoroalkylalkylcarboxylic acids according to the invention are manufactured by hydrolysing perfluoroalkylalkyl nitriles of the formula

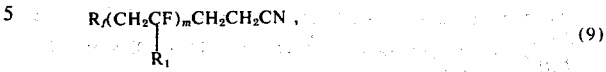  (9)

wherein $R_f$ is an unbranched or branched perfluoroalkyl radical with 3 to 18 carbon atoms, $R_1$ is hydrogen or fluorine, and m is a whole number from 1 to 3, in the presence of inorganic or organic acids.

The perfluoroalkylalkyl nitriles that are preferably used have the formulae

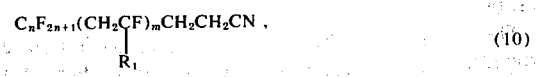  (10)

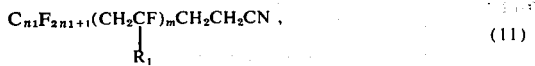  (11)

$C_{n1}F_{2n1+1}CH_2CF_2CH_2CH_2CN,$  (12)

$C_{n1}F_{2n1+1}(CH_2CF_2)_2CH_2CH_2CN,$  (13)

$C_{n1}F_{2n1+1}CH_2CHF\ CH_2CH_2CN$ and  (14)

$C_{n1}F_{2n1+1}(CH_2CHF)_2CH_2CH_2CN,$  (15)

wherein $n$, $n_1$, $m$ and $R_1$ have the indicated meanings.

Suitable acids are, for example, sulphuric acid, hydrochloric acid, formic acid, or acetic acid.

The reaction is carried out at temperatures of about 50° to 200°C, preferably 80° to 180°C, and either in a solvent or without a solvent. Preferably no solvent is used. The reaction mixture is ordinarily in the form of an emulsion of the perfluoroalkylalkyl nitrile in the acid.

The acid is simultaneously reaction medium and reagent. The amount of it is therefore expediently so chosen that a multiple molar surplus is used, based on the perfluoroalkylalkyl nitrile. The reaction time can be about 5 to 30, preferably 10 to 20, hours.

The perfluoroalkylalkyl nitriles used as starting products are obtained by addition of vinylidene or vinyl fluoride, and subsequently of ethylene, to perfluoroalkyl iodides of the formula $R_fI$, and by reaction in a further reaction step with a metal cyanide.

The compounds according to the invention are suitable for producing oil and water repellent finishes on porous and non-porous substrates, also for obtaining soil release and antisoiling effects. In addition they can be used as intermediates for the manufacture of further valuable fluorinated end products. These end products are obtained for example, by a modification of the carboxyl group by known chemical reactions.

By porous substrates are meant, for example, leather, paper and wood, but preferably textile fabrics, whereas suitable non-porous materials are surfaces of glass, metal, and plastic. The compounds according to the invention can also be used, for example, as additives for oil and lubricants for preventing wear and corrosion, or as lubricants, as additives for polishes and waxes, and as surface-active assistants.

The compounds according to the invention can be used in particular for finishing textile fabrics, for example those made from natural and regenerated cellulose, e.g. cotton, linen, staple fibre, or cellulose acetate, also those made from wool, synthetic polyamides, polyesters, polypropylene and polyacrylonitrile, and also the corresponding fibre blends.

The textile fabrics can be in any desired form of processing, for example as fibres, threads, tops, woven and knitted fabrics.

The compounds according to the invention are applied from solvent liquors by the immersion process, also by padding, spraying, slop-padding, immersion in a melt, spraying with heat fixing or also by transfer from an auxiliary material (paper, foil) accompanied by the application of heat.

The compounds according to the invention are applied in amounts of about 0.05 to 10, preferably 0.1 to 5, percent by weights, based on the weight of the substrates.

The following Examples will serve to illustrate the invention but do not imply any limitation thereof. Parts and percentages are by weight.

EXAMPLE 1

35 g of the nitrile of the formula $CF_3(CF_2)_n(CH_2CF_2)_oCH_2CH_2CN$ ($n = 5, 7, 9; o = 1, 2, 3$) are emulsified in 100 ml of sulphuric acid and heated to 140°C over the course of 20 hours. The emulsion is then poured on ice. The aqueous phase is then extracted with diethyl ether and the ethereal phase is dried over sodium sulphate. The solvent is distilled off to yield the acid of the formula (101) $CF_3(CF_2)_n(CH_2CF_2)_oCH_2CH_2COOH$.

Yield: 34.2 g of white powder.
Melting point: 93°–95°C.
Acid titer: 56.7 g of NaOH/kg of acid.

EXAMPLE 2

39 g of the nitrile of the formula $CF_3(CF_2)_nCH_2CHF\ CH_2CH_2CN$ ($n = 5, 7, 9$)

are emulsified in 100 ml of sulphuric acid (75%). The emulsion is then poured on ice. The aqueous phase is then extracted with diethyl ether and the ethereal phase is dried over sodium sulphate. The solvent is distilled off to yield the acid of the formula (102) $CF_3(CF_2)_nCH_2CHFCH_2CH_2COOH$.

Yield: 36.6 g of light brown powder.
Melting point: 67°–77°C.
Acid titer: 63 g of NaOH/kg of acid.

EXAMPLE 3

Cotton, cotton/polyester (35/66) and polyamide fabrics are thoroughly impregnated with a 1% solution of the compounds of the formulae (101) and (102), squeezed out, and left to dry in the air. In the 3-M test the treated fabrics exhibit oil repellencies of 100 to 110 (untreated fabric: 0). (3-M oil repellency test, E. J. Grajeck, W. H. Peterson, Textile Research Journal 32, 320–331, 1960. The test is carried out with heptane/nujol mixtures and evaluated with ratings from 0 to 150; 150 is the rating that indicates the best oil repellency).

I claim:

1. A perfluoroalkylalkylcarboxylic acid of the formula

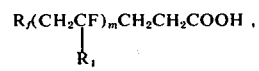

wherein $R_f$ is an unbranched or branched perfluoroalkyl radical with 3 to 18 carbon atoms, $R_1$ is hydrogen or fluorine, and $m$ is a whole number from 1 to 3.

2. A perfluoroalkylalkylcarboxylic acid according to claim 1, of the formula

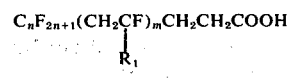

wherein $R_1$ is hydrogen or fluorine, $n$ is a whole number from 3 to 14, and $m$ is a whole number from 1 to 3.

3. A perfluoroalkylalkylcarboxylic acid according to claim 2, of the formula

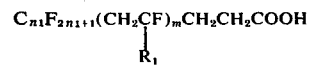

wherein $R_1$ and $m$ have the meanings given in claim 2 and $n_1$ is a whole number from 4 to 12.

4. A perfluoroalkylalkylcarboxylic acid according to claim 3, of the formula

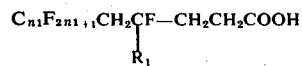

wherein $R_1$ and $n_1$ have the meanings given in claim 3.

5. A perfluoroalkylalkylcarboxylic acid according to claim 3, of the formulae $C_{n_1}F_{2n_1+1}CH_2CHFCH_2CH_2COOH$ and $C_{n_1}F_{2n_1+1}CH_2CF_2CH_2CH_2COOH$ wherein $n_1$ is a whole number from 4 to 12.

6. A perfluoroalkylalkylcarboxylic acid according to claim 3, of the formulae $C_{n_1}F_{2n_1+1}(CH_2CHF)_2CH_2CH_2COOH$ and $C_{n_1}F_{2n_1+1}(CH_2CF_2)_2CH_2CH_2COOH$ wherein $n_1$ is a whole number from 4 to 12.

* * * * *